United States Patent [19]

Hellerbach et al.

[11] 4,005,085
[45] Jan. 25, 1977

[54] BENZOPHENONE DERIVATIVES

[75] Inventors: Joseph Hellerbach; André Szente, both of Basel, Switzerland

[73] Assignee: Hoffmann-La Roche Inc., Nutley, N.J.

[22] Filed: Nov. 22, 1974

[21] Appl. No.: 522,678

[30] Foreign Application Priority Data

Nov. 15, 1973 Switzerland .................. 16101/73

[52] U.S. Cl. .................. 260/247.2 B; 260/268 R; 260/293.74; 260/326.47; 260/471 C; 424/263; 424/248.54; 424/309

[51] Int. Cl.[2] .................. C07D 95/00

[58] Field of Search .............. 260/471 C, 247.2 B, 260/268 R, 326.47, 293.74

[56] References Cited

UNITED STATES PATENTS

| | | | |
|---|---|---|---|
| 3,100,222 | 8/1963 | Beaver | 260/471 C |
| 3,160,648 | 12/1964 | O'Brochta et al. | 260/471 C |
| 3,927,010 | 12/1975 | Hellerbach et al. | 260/471 C |

Primary Examiner—Paul J. Killos
Attorney, Agent, or Firm—Samuel L. Welt; Bernard S. Leon; Frank P. Hoffman

[57] ABSTRACT

Benzophenone derivatives are produced which have the formula

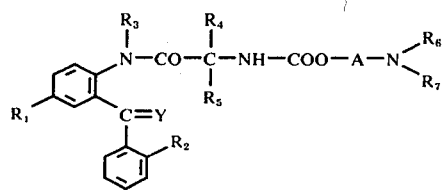

wherein $R_1$ signifies hydrogen, nitro, halogen or trifluoromethyl; $R_2$ represents hydrogen or halogen; $R_3$, $R_4$ and $R_5$ are the same or different and signify hydrogen or lower alkyl; $R_6$ and $R_7$ each represent lower alkyl or together with the nitrogen atom form a morpholino, 4-(lower alkyl)-1-piperazinyl, 1-pyrrolidinyl or piperidino group, A signifies an alkylene group with 2 to 8 C atoms and Y represents oxygen or a group

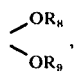

$R_8$ and $R_9$ each signifying lower alkyl or together signifying lower alkylene.

The benzophenone derivatives and their pharmaceutically acceptable salts exhibit sedative, anti-convulsant, muscle relaxant and anxiolytic activities.

Also provided are methods for the preparation of these compounds.

6 Claims, No Drawings

BENZOPHENONE DERIVATIVES

DESCRIPTION OF THE INVENTION

This invention relates to pharmacologically active benzophenone derivatives. The chemical structure of these compounds may be depicted by the following formula

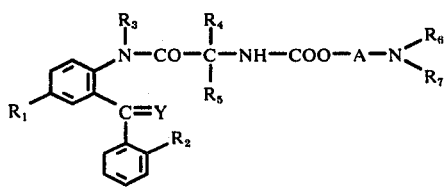
I wherein $R_1$ signifies hydrogen, nitro, halogen or trifluoromethyl, $R_2$ represents hydrogen or halogen, the residues $R_3$, $R_4$ and $R_5$ are the same or different and signify hydrogen or lower alkyl, $R_6$ and $R_7$ each represent lower alkyl or together with the nitrogen atom form a morpholino, 4-(lower alkyl)-1-piperazinyl, 1-pyrrolidinyl or piperidino group, A signifies an alkylene group with 2 to 8 C atoms and Y represents oxygen or a group

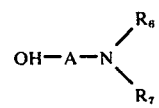

$R_8$ and $R_9$ each signifying lower alkyl or together signifying lower alkylene.

The expression "lower alkyl" denotes a straight-chain or branched hydrocarbon with 1 to 4 carbon atoms such as methyl, ethyl, n-propyl, isobutyl and the like. The term "lower alkylene" relates to straight or branched alkylene groups with 2 to 6 carbon atoms. Unless otherwise stated, by "halogen" the four halogens fluorine, chlorine, bromine and iodine are understood.

Of the compounds of the formula I, there are preferred those in which the alkylene group A has 2 – 6, preferably 2 – 4 carbon atoms, $R_1$ is halogen or nitro, $R_3$ is hydrogen or methyl, $R_4$ and $R_5$ are hydrogen, $R_6$ and $R_7$ signify alkyl or together with the nitrogen atom form morpholino or peripidino and Y represents oxygen or dialkoxy.

More especially preferred are those compounds according to formula I in which A is trimethylene, $R_1$ represents nitro or chlorine, $R_2$ signifies chlorine or fluorine, $R_3$ is methyl, $R_4$ and $R_5$ signify hydrogen, $R_6$ and $R_7$ together with the nitrogen atom form morpholino and Y is oxygen.

The compounds of the formula I and their salts can be manufactured in accordance with the invention by:

a. reacting an amine of the general formula

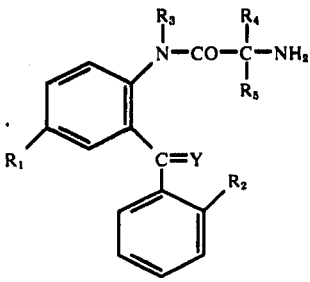
II wherein $R_1$, $R_2$, $R_3$, $R_4$, $R_5$ and Y are as above, in the presence of phosgene with an aminoalcohol of the general formula

III wherein A, $R_6$ and $R_7$ are as above, or b. for the manufacture of a compound of formula I in which Y represents an oxygen atom, hydrolyzing a compound of the general formula

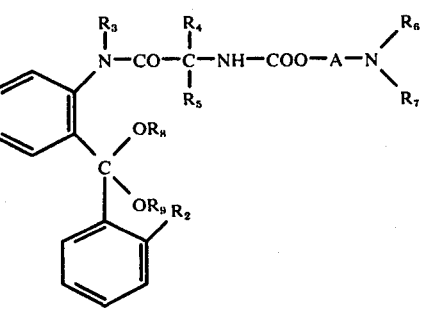
IV wherein $R_1$, $R_2$, $R_3$, $R_4$, $R_5$, $R_6$, $R_7$, $R_8$, $R_9$ and A are as above, or c. for the manufacture of a compound of formula I in which Y represents a group of the formula $$\begin{array}{c} OR_8 \\ \diagdown \\ OR_9 \end{array}$$

in which $R_8$ and $R_9$ are as above, reesterifying a lower alkyl ester of a carboxylic acid of the general formula

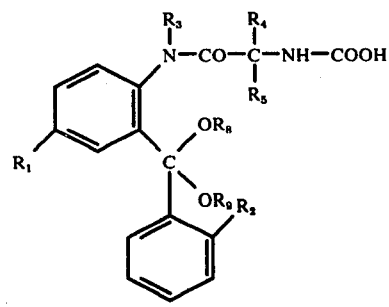
V wherein $R_1$, $R_2$, $R_3$, $R_4$, $R_5$, $R_8$ and $R_9$ are as above, by treatment with an aminoalcohol of formula III above, or d. for the manufacture of compounds of the formula I in which Y signifies oxygen, reacting a benzodiazepine derivative of the general formula

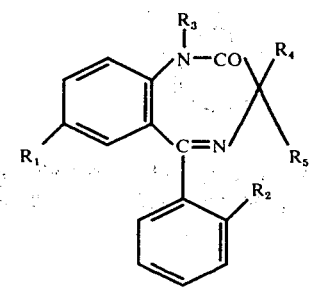

wherein $R_1$, $R_2$, $R_3$, $R_4$ and $R_5$ are as above, with phosgene and aminoalcohol of the general formula III and, if desired, f. converting an obtained compound of the formula I into an acid addition salt or converting an acid addition salt obtained into the free base of formula I.

According to embodiment (a) of the present process, compounds of formula I are manufactured by reacting an amine of formula II in the presence of phosgene with an aminoalcohol of formula III. The reaction is expediently carried out in a suitable inert organic solvent and in the presence of a proton acceptor such as sodium carbonate. Examples of solvents which can be used are aromatic hydrocarbons (e.g., benzene or toluene), halogenated hydrocarbons (e.g., methylene chloride, chloroform or carbon tetrachloride) and ethers (e.g., diethyl ether or dioxane). In carrying out this reaction, an amine of formula II or an aminoalcohol of formula III may firstly be phosgenated in the cold and the other reaction partner then added thereto. The reaction mixture is subsequently maintained for 1 to 5 hours at a temperature between room temperature and the reflux temperature of the mixture, the reflux temperature being preferred.

According to embodiment (b) of the present process, compounds of formula I in which Y represents an oxygen atom are manufactured by hydrolyzing a compound of formula IV hereinbefore. The hydrolysis can be carried out, for example, by dissolving a compound of formula IV at room temperature in an excess of a dilute, preferably in mineral acid, preferably hydrochloric acid, and optionally warming the solution for a short time. There is thus obtained a salt of a compound of formula I in which Y represents an oxygen atom from which the base can be liberated in the usual manner.

According to embodiment (c) of the present process, compounds of formula I in which Y represents a group of the formula

wherein $R_8$ and $R_9$ are as above, are manufactured by reacting a lower alkyl ester of a carboxylic acid of formula V hereinbefore with an aminoalcohol of formula III hereinbefore. This reaction is expediently carried out in an inert or organic solvent such as an aromatic hydrocarbon (e.g., benzene or toluene) or a halogenated hydrocarbon (e.g., methylene chloride). The reaction is preferably carried out at a temperature between 0° C. and the reflux temperature of the reaction mixture. The reaction can be carried out in the presence of a catalyst such as sodium, sodium methylate or the like.

According to embodiment (d) of the present process, compounds of formula I in which Y represents an oxygen atom are manufactured by reacting a benzodiazepine derivative of formula VI hereinbefore with phosgene and an amino-alcohol of formula III hereinbefore. In carrying out this reaction, a benzodiazepine derivative of formula VI is conveniently dissolved in an inert organic solvent and then treated with phosgene and an aminoalcohol of formula III. It is advisable to carry out this reaction in the presence of a proton acceptor such as sodium carbonate. In order to complete the reaction, the reaction mixture is heated to reflux for some time (between 2 and 6 hours). Examples of solvents which can be used in this embodiment of the process are the solvents mentioned hereinbefore in connection with embodiment (a).

The compounds of formula I can be converted into acid addition salts, especially pharmaceutically acceptable acid addition salts, according to generally known methods by treatment with inorganic or organic acids. Examples of inorganic and organic acids which form pharmaceutically acceptable salts are hydrochloric acid, hydrobromic acid, sulfuric acid, acetic acid, succinic acid, maleic acid, p-toluenesulfonic acid, etc.

The starting materials of formulae II, III, IV and VI hereinbefore are known or can be prepared in accordance with methods known per se.

The starting materials of formula IV can be prepared according to embodiment (a) of the present process.

Lower alkyl esters of carboxylic acids of formula V are either known or can be prepared in a manner known per se.

The compounds of formula I hereinbefore and their pharmaceutically acceptable acid addition salts possess sedative, anti-convulsant, muscle-relaxant and/or anxiolytic activity.

The anti-convulsant activity is demonstrated when mice to which compounds of formula I or their salts have been administered are subjected to the pentamethylenetetrazole test. For example, in the test for anti-convulsant activity in the pentetrazole test according to the method of Orloff (Proc. Soc. Exptl. Biol. Med. 70, 254–257, 1949), 3-morpholino-propyl-{[[4-chloro-2-(o-fluorobenzoyl) phenyl]-methylcarbamoyl]-methyl} carbamate, which has an $LD_{50}$ between 500 and 1000 mg/kg p.o. in mice, has an APR 2.0 of 3.8 ± 0.2 mg/kg. p.o. [by APR 2.0 is understood that dose in mg/kg. of an anti-convulsant which causes double the pentetrazole dose in comparison to an untreated group]. In the same test, 3-morpholino-propyl-{[[2-(o-chlorobenzoyl)-4-nitrophenyl]methylcarbamoyl]-methyl}carbamate, which has an $LD_{50}$ between 500 and 1000 mg/kg. p.o., has an APR 2.0 of 7.06 ± 0.6 mg/kg. p.o. In contrast, phenobarbital, a well-known anti-convulsant, has an APR 2.0 of 30 mg/kg.

The muscle-relaxant activity can be demonstrated in the test on the rotating rod. For example, the aforementioned 3-morpholinopropyl-{[[4-chloro-2-(o-fluorobenzoyl)phenyl]-methylcarbamoyl]-methyl}carbamate has a $HD_{50}$ of 7.33 ± 0.60 mg/kg. p.o. upon administration to mice and 3-morpholinopropyl{[[2-(o-chlorobenzoyl)-4-nitrophenyl]methylcarbamoyl]-methyl}carbamate has a $HD_{50}$ of 8.50 ± 0.76 mg/kg. p.o.

The compounds of formula I and their pharmaceutically acceptable acid addition salts may accordingly be used as medicaments; for example, in the form of pharmaceutical preparations which contain them in association with a compatible pharmaceutical carrier. This carrier may be an organic or inorganic carrier material suitable for enteral or parenteral administration such as, for example, water, gelatin, lactose, starch, magnesium stearate, talc, vegetable oils, gum arabic, polyalkyleneglycols, petroleum jelly and the like. The pharmaceutical preparations can be made up in solid form (e.g., as tablets, dragees, suppositories or capsules) or in liquid form (e.g., as solutions, suspensions or emulsions). The pharmaceutical preparations may be sterilized and/or may contain adjuvants such as preserving, stabilizing, wetting or emulsifying agents, salts for variation of the osmotic pressure or buffers. The pharmaceutical preparations can also contain other therapeutically valuable substances. Expedient pharmaceutical dosage forms contain from ca 1 to 200 mg. of a compound of formula I. The dosage will, of course, depend on individual requirements, but, in the case of mammals, a dosage of from about 0.1 mg/kg. to 5 mg/kg. p.o. or 0.01 mg/kg. to 0.5 mg/kg. i.v. per day is preferred.

The following Examples illustrate but do not limit the present invention. In these Examples, all temperatures are stated in degrees Celsius.

EXAMPLE 1

145 G. of morpholinopropanol freshly distilled over sodium are treated with 14 g. of sodium methylate, 20 ml. of morpholinopropanol being subsequently distilled off in vacuo. 25 G. of the residue obtained are added to a solution of 5 g. of methyl { [[4-chloro-2-($\alpha$,$\alpha$-dimethoxy-o-fluorobenzyl)phenyl]-methylcarbamoyl]methyl}carbamate in 12 g. of absolute methylene chloride. The mixture is maintained at 55° C. in a rotary evaporator for 12 hours and is then treated with methylene chloride/water. The methylene chloride phase is washed ten times with water, dried over sodium sulfate, filtered and concentrated. There is obtained crude 3-morpholinopropyl-{[[4-chloro-2-($\alpha$,$\alpha$-dimethoxy-o-fluorobenzyl)phenyl]methylcarbamoyl]methyl}carbamate.

The foregoing product is dissolved in 100 ml. of 1N hydrochloric acid at room temperature. The aqueous solution is washed five times with benzene, made alkaline with sodium carbonate and extracted three times with ethyl acetate. The ethyl acetate extracts are dried over sodium sulfate, filtered and concentrated. There is obtained as the residue 3-morpholinopropyl{[[4-chloro-2-(o-fluorobenzoyl)phenyl]-methylcarbamoyl] methyl} carbamate which melts at 72°–76° C. After crystallization from ethanol/n-hexane. The corresponding hydrochloride, an amorphous substance, is obtained in the usual manner.

EXAMPLE 2

22 G. of 7-chloro-1,3-dihydro-1-methyl-5-(o-fluorophenyl)-2H-1,4-benzodiazepin-2-one are dissolved in 250 ml. of absolute methylene chloride and treated with 13 g. of phosgene, 10.5 g. of morpholinopropanol and 30 g. of sodium bicarbonate. The mixture is heated at reflux for 4 hours; at the end of the first and third hour a further 13 g. of phosgene, 10 g. of morpholinopropanol and 30 g. of sodium bicarbonate being added each time. The mixture is then washed several times with 10% sodium carbonate solution, dried over sodium sulfate, filtered and concentrated. The residue is taken up in benzene and the benzene solution washed ten times with water and then extracted with 1N hydrochloric acid. The hydrochloric acid extract is made alkaline with sodium carbonate and extracted with ethyl acetate. The ethyl acetate extract is washed four times with water, dried over sodium sulfate, filtered and concentrated. There is obtained as the residue 3-morpholinopropyl{[[4-chloro-2-(o-fluorobenzoyl)-phenyl]-methylcarbamoyl]methyl}carbamate which is identical with the product obtained according to Example 1 and which melts at 75° C. after crystallization from ethanol/n-hexane.

EXAMPLE 3

55 G. of benzyl {[[4-chloro-2-(o-fluorobenzoyl)-phenyl]-methylcarbamoyl]methyl}carbamate are stirred with 250 ml. of 30% hydrobromic acid in glacial acetic acid for 45 minutes at room temperature. The mixture is concentrated on a rotary evaporator, treated with absolute ether, filtered and washed with ether. After repeated concentration, there is obtained crude, hydroscopic 2-amino-4'-chloro-2'-(o-fluorobenzoyl)-N-methyl-acetanilide hydrobromide.

28 G. of phosgene are dissolved at −10° C. in 300 ml. of absolute methylene chloride. The solution is treated with 36 g. of morpholinopropanol, the 2-amino-4'-chloro-2'-(o-fluorobenzoyl)-N-methyl-acetanilide hydrobromide obtained according to the preceding paragraph and 91 g. of sodium carbonate and the mixture is stirred at room temperature for 3 hours. The residue obtained after concentration is treated with benzene/water and the aqueous phase is separated. The benzene phase is extracted with dilute hydrochloric acid, the hydrochloric acid extracts are washed several times with benzene, made alkaline with aqueous sodium carbonate solution and extracted with ethyl acetate. The ethyl acetate extract is dried over sodium sulfate, filtered and concentrated. There is obtained as the residue 3-morpholinopropyl{[[4-chloro-2-(o-fluorobenzoyl)phenyl]methylcarbamoyl] methyl}carbamate which is identical with the product obtained according to Examples 1 and 2 and which melts at 75° C. after crystallization from ether/n-hexane.

EXAMPLE 4

In a manner analogous to that described in the first paragraph of Example 1, but using morpholinoethanol in place of morpholinopropanol, there is obtained crude 2-morpholinoethyl{ [[4-chloro-2-($\alpha$,$\alpha$-dimethoxy-o-fluorobenzyl)phenyl]methylcarbamoyl]methyl}carbamate.

This compound is subjected to an analogous procedure to that described in the second paragraph of Example 1 to give 2-morpholinoethyl{[[4-chloro-2-(o-fluorobenzoyl)phenyl]methylcarbamoyl]methyl}carbamate which melts at 67°–70° C. after crystallization from ether/n-hexane.

EXAMPLE 5

In a manner analogous to that described in the second paragraph of Example 3, but using morpholinobutanol in place of morpholinopropanol, there is obtained 4-morpholinobutyl-{[[4-chloro-2-(o-fluorobenzoyl)phenyl]methylcarbamoyl]-methyl}carbamate which melts at 91° C. after crystallization from ether/n-hexane.

EXAMPLE 6

In a manner analogous to that described in the first paragraph of Example 1, but using morpholinohexanol in place of morpholinopropanol, there is obtained crude 6-morpholinohexyl{[[4-chloro-2-($\alpha$,$\alpha$-dimethoxy-o-fluorobenzyl)phenyl]methylcarbamoyl]methyl}carbamate.

This product is subjected to an analogous procedure to that described in the second paragraph of Example 1 to give 6-morpholinohexyl{[[4-chloro-2-(o-fluorobenzoyl)phenyl]methylcarbamoyl]methyl}carbamate which melts at 61°-63° C. after crystallization from ether/n-hexane.

EXAMPLE 7

In a manner analogous to that described in the second paragraph of Example 3, but using piperidinopropanol in place of morpholinopropanol, there is obtained 3-piperidinopropyl-{[[4-chloro-2-(o-fluorobenzoyl)phenyl]methylcarbamoyl]-methyl}carbamate which melts at 63°-65° C. after crystallization from ether/n-hexane.

EXAMPLE 8

In a manner analogous to that described in the first paragraph of Example 1, but using diethylaminopropanol in place of morpholinopropanol, there is obtained crude 3-diethylaminopropyl{[[4-chloro-2-($\alpha$,$\alpha$-dimethoxy-o-fluorobenzyl)phenyl]methylcarbamoyl]methyl} carbamate.

This product is subjected to an analogous procedure to that described in the second paragraph of Example 1 to give 3-diethylaminopropyl{[[4-chloro-2-(o-fluorobenzoyl)phenyl]methylcarbamoyl]methyl}carbamate which melts at 55°-57° C. after crystallization from ether/n-hexane. The corresponding hydrochloride melts at 122°-126° C. after crystallization from methylene chloride/ethyl acetate.

EXAMPLE 9

In a manner analogous to that described in the first paragraph of Example 1, but using diethylaminoethanol in place of morpholinopropanol, there is obtained crude 2-diethylaminoethyl{[[4-chloro-2-($\alpha$,$\alpha$-dimethoxy-o-fluorobenzyl)phenyl]methylcarbamoyl]methyl}carbamate.

This product is subjected to an analogous procedure to that described in the second paragraph of Example 1 to give 2-diethylaminoethyl{[[4-chloro-2-(o-fluorobenzoyl)phenyl]methylcarbamoyl]methyl}carbamate which melts at 88°-90° C. after crystallization from ether/n-hexane.

EXAMPLE 10

In a manner analogous to that described in Example 2, but using 7-nitro-1,3-dihydro-1-methyl-5-(o-chlorophenyl)-2H-1,4-benzodiazepin-2-one, there is obtained 3-morpholinopropyl{[[2-o-chlorobenzoyl)-4-nitrophenyl]methylcarbamoyl]methyl} carbamate which melts at 127°-128° C. after crystallization from ethanol/n-hexane. The corresponding hydrochloride melts at 165° C. after crystallization from methylene chloride/ethyl acetate.

EXAMPLE 11

In a manner analogous to that described in the first paragraph of Example 1, but using methyl{[[4-chloro-2-($\alpha$,$\alpha$-diethoxybenzyl)phenyl]methylcarbamoyl]methyl}carbamate in place of methyl{[[4-chloro-2-($\alpha$,$\alpha$-dimethoxy-o-fluorobenzyl)phenyl]methylcarbamoyl]methyl}carbamate, there is obtained crude 3-morpholinopropyl{[[4-chloro-2-($\alpha$,$\alpha$-diethoxybenzyl)phenyl]methylcarbamoyl]methyl} carbamate which melts at 110°-111° C. after crystallization from ether/petroleum ether.

This product is subjected to an analogous procedure to that described in the second paragraph of Example 1 to give 3-morpholinopropyl{-[(2-benzoyl-4-chlorophenyl)methylcarbamoyl]methyl}carbamate. The corresponding hydrochloride melts at 99°-103° C. after treatment with n-hexane.

The following Examples illustrate typical pharmaceutical preparations containing the basically-substituted benzophenone derivatives provided by the present invention:

Example A
Tablets of the following composition are manufactured:

| | |
|---|---|
| 3-morpholinopropyl{[[4-chloro-2-(o-fluorobenzoyl)-phenyl]methylcarbamoyl]methyl}carbamate or 3-morpholinopropyl{[[2-(o-chlorobenzoyl)-4-nitrophenyl]methylcarbamoyl]methyl} carbamate | 2.0 mg. |
| Lactose | 95.0 mg. |
| Maize starch | 50.0 mg. |
| Talc | 2.7 mg. |
| Magnesium stearate | 0.3 mg. |
| Total Weight | 150.0 mg. |

The active ingredient and the adjuvants are mixed and the mixture obtained is pressed to tablets.

Example B
Tablets of the following composition are manufactured:

| | |
|---|---|
| 3-morpholinopropyl{[[4-chloro-2-(o-fluorobenzoyl)-phenyl]methylcarbamoyl] methyl} carbamate or 3-morpholinopropyl{[[2-(o-chlorobenzoyl)-4-nitrophenyl]methylcarbamoyl] methyl} carbamate | 5.0 mg. |
| Lactose | 120.0 mg. |
| Maize starch | 60.0 mg. |
| Kollidon | 10.0 mg. |
| Talc | 4.6 mg. |
| Magnesium stearate | 0.4 mg. |
| Total Weight | 200.0 mg. |

The active ingredient and the adjuvants are mixed and the mixture obtained is pressed to tablets.

Example C
Capsules containing the following ingredients are manufactured:

| | |
|---|---|
| 3-morpholinopropyl{[[4-chloro-2-(o-fluorobenzoyl)phenyl]methylcarbamoyl]methyl} carbamate | 10.0 mg. |
| Lactose | 101.0 mg. |
| Maize starch | 20.0 mg. |
| Talc | 9.0 mg. |
| Total contents of capsule | 140.0 mg. |

The active ingredients and the adjuvants are mixed and the mixture is mechanically filled into hard gelatin capsules.

Example D
Suppositories of the following composition are manufactured:
3-morpholinopropyl{[[4-chloro-2-(o-fluoro- -continued

| Example D | |
|---|---|
| benzoyl)phenyl]methylcarbamoyl]methyl} carbamate | 10.0 mg. |
| Cremophor 1.0% | |
| Propyleneglycol monostearate 4.5% | q.s. for the total weight of 1 suppository |
| Witepsol H 94.5% | |

The adjuvants are melted together and the active ingredient is added and mixed until a uniform mixture is obtained. This mixture is then poured into suppository molds of suitable size. After cooling, the suppositories are removed from the molds and individually packed in metal foil.

EXAMPLE E

10 Mg. of 3-morpholinopropyl {[[4-chloro-2-(o-fluorobenzoyl)phenyl]methylcarbamoyl]methyl}carbamate hydrochloride (prepared from an aseptically filtered solution of this substance) and 5 ml. of aseptically filtered water for injection purposes are filled into ampules under aseptic conditions. The ampuls are then sealed under aseptic conditions.

What is claimed:

1. A compound of the formula

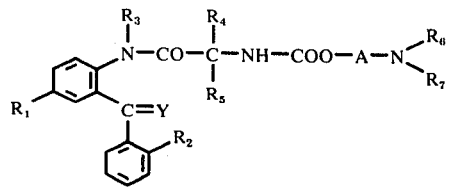

wherein
 $R_1$ is selected from the group consisting of hydrogen, nitro, halogen and trifluoromethyl;
 $R_2$ is selected from the group consisting of hydrogen and halogen;
 $R_3$, $R_4$ and $R_5$ are selected from the group consisting of hydrogen and lower alkyl;
 $R_6$ and $R_7$ are lower alkyl or together with the nitrogen atom are a morpholino, 4-(lower alkyl)-1-piperazinyl, 1-pyrrolidinyl or piperidino group;
 A is a $C_2$–$C_8$ alkylene group; and Y is selected from the group consisting of oxygen and the group $$\diagup^{OR_8}_{\diagdown OR_9}$$

wherein
 $R_8$ and $R_9$ are lower alkyl or together are lower alkylene;
and the pharmaceutically acceptable acid addition salts thereof.

2. The compound of claim 1 wherein
 A is a $C_2$–$C_6$ alkylene group;
 $R_1$ is selected from the group consisting of halogen and nitro;
 $R_3$ is selected from the group consisting of hydrogen and methyl;
 $R_4$ and $R_5$ are hydrogen;
 $R_6$ and $R_7$ are lower alkyl or together with the nitrogen atom from a morpholino or piperidino group;
 and Y is selected from the group consisting of oxygen and a dialkoxy group.

3. The compound of claim 2 wherein
 A is a $C_2$–$C_4$ alkylene group;
 $R_1$ is selected from the group consisting of chlorine and nitro;
 $R_2$ is selected from the group consisting of chlorine and fluorine;
 $R_3$ is methyl;
 $R_6$ and $R_7$ together with the nitrogen atom from a morpholino group; and
 Y is oxygen 4. A compound of the formula 3-Morpholinopropyl[4-chloro-2-(o-fluorobenzoyl)-phenyl]-methylcarbamoyl-methylcarbamate.

5. A compound of the formula 3-Morpholinopropyl[2-(o-chlorobenzoyl)-4-nitrophenyl]methylcarbamoyl-methylcarbamate.

6. A process for producing a compound of the formula

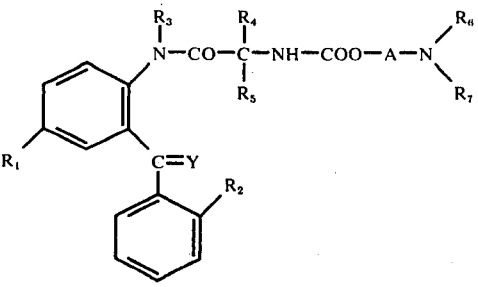

wherein
 $R_1$ is selected from the group consisting of hydrogen, nitro, halogen and trifluoromethyl;
 $R_2$ is selected from the group consisting of hydrogen and halogen;
 $R_3$, $R_4$ and $R_5$ are selected from the group consisting of hydrogen and lower alkyl;
 $R_6$ and $R_7$ are lower alkyl or together with the nitrogen atom are a morpholino, 4-(lower alkyl)-1-piperazinyl, 1-pyrrolidinyl or piperidino group;
 A is a $C_2$–$C_8$ alkylene group; and
 Y is selected from the group consisting of oxygen and the group

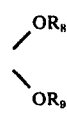

wherein $R_8$ and $R_9$ are lower alkyl or together are lower alkylene
which comprises reacting a compound of the formula

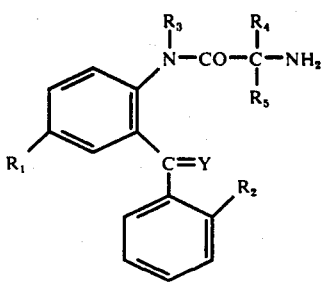

wherein
- $R_1$ is selected from the group consisting of hydrogen, nitro, halogen and trifluoromethyl;
- $R_2$ is selected from the group consisting of hydrogen and halogen;
- $R_3$, $R_4$ and $R_5$ are selected from the group consisting of hydrogen and lower alkyl; and
- Y is selected from the group consisting of oxygen and the group

wherein $R_8$ and $R_9$ are lower alkyl or together are lower alkylene;
in the presence of phosgene in an organic solvent and in the presence of a proton acceptor with a compound of the formula

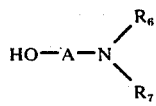

wherein $R_6$ and $R_7$ are lower alkyl or together with the nitrogen atom are a morpholino, 4-(lower alkyl)-1-piperazinyl, 1-pyrrolidinyl or piperidino group; and A is a $C_2$–$C_8$ alkylene group, the reaction mixture being maintained for 1 to 5 hours at a temperature between room temperature and reflux temperature.

* * * * *